(12) United States Patent
Harod

(10) Patent No.: US 6,358,516 B1
(45) Date of Patent: Mar. 19, 2002

(54) ONE-STEP SYSTEM FOR CLEANSING, CONDITIONING, AND TREATING THE SKIN

(76) Inventor: Norris R. Harod, 4052 Indian Creek Rd., Martinez, GA (US) 30907-2234

( * ) Notice: Subject to any disclaimer, the term of this patent is extended or adjusted under 35 U.S.C. 154(b) by 0 days.

(21) Appl. No.: 09/471,538

(22) Filed: Dec. 23, 1999

Related U.S. Application Data

(63) Continuation-in-part of application No. 09/137,637, filed on Aug. 21, 1998.

(51) Int. Cl.$^7$ .......................... A61K 6/00; A61K 39/385
(52) U.S. Cl. ..................... 424/401; 424/195.1; 514/844
(58) Field of Search ................................ 424/404, 402, 424/401, 195.1; 514/844

(56) References Cited

U.S. PATENT DOCUMENTS

| | | | | |
|---|---|---|---|---|
| 4,847,069 A | * | 7/1989 | Bissett et al. ................... | 424/47 |
| 5,534,265 A | * | 7/1996 | Fowler et al. ................... | 424/489 |
| 5,635,469 A | * | 6/1997 | Fowler et al. ................... | 510/406 |
| 5,648,083 A | * | 7/1997 | Blieszner et al. ............... | 424/402 |
| 5,702,992 A | * | 12/1997 | Martin et al. .................... | 442/123 |
| 5,720,961 A | * | 2/1998 | Fowler et al. ................... | 424/401 |
| 6,036,965 A | * | 3/2000 | Gubernick et al. .............. | 424/401 |
| 6,153,208 A | * | 11/2000 | McAtee et al. .................. | 424/402 |
| 6,183,766 B1 | * | 2/2001 | Sine et al. ....................... | 424/405 |

* cited by examiner

*Primary Examiner*—William R. A. Jarvis
*Assistant Examiner*—Vickie Kim
(74) *Attorney, Agent, or Firm*—Maria Reichmanis

(57) ABSTRACT

A skin care system that cleanses, therapeutically conditions, and provides additional beneficial treatment to the skin in a simple, one-step application that air dries quickly. The system is implemented as a skin care kit in the form of a container with a plurality of pre-moistened soft cloths therein. The cloths are impregnated with a treatment composition that contains a plurality of ingredients selected from the following groups: (a) surfactants, (b) anti-inflammatory agents, (c) non-foaming agents, (d) cell-growth-promoting agents, (e) immune system-enhancing agents, (f) antimicrobial agents, (g) absorption facilitating agents, (h) humectants and emollients, (i) free radical-scavenging agents, (j) healing promoting agents, and (optionally) preservatives and fragrances. In use, the cloths gently cleanse the skin, trap and carry away dirt and soil, and deposit beneficial ingredients that coat and are absorbed into the skin. The system is portable, disposable, easily stored, and can be partially used and resealed for further use.

30 Claims, 2 Drawing Sheets

ONE-STEP SYSTEM FOR CLEANSING, CONDITIONING, AND TREATING THE SKIN

This application is a continuation-in-part of copending application(s) application Ser. No. 09/137,637 filed on Aug. 21, 1998.

BACKGROUND OF THE INVENTION

1. Field of the Invention

The present invention relates to a system for cleansing, conditioning, and treating the skin. In particular, the present invention relates to a one-step system that delivers a combination of surfactants, humectants, emollients, antimicrobial agents, and other beneficial ingredients in a no-rinse, self-drying formulation that promotes effective absorption into the surface layers of the skin.

2. Discussion of Background

Many different types of products are used in cleansing and conditioning the skin: solid and liquid soaps, surfactants, humectants, moisturizers, emollients, astringents, deodorants, and antimicrobial agents, and other compositions which provide the desired beneficial effects. The normal method of cleansing the skin with soap and water originated in about 2000 BC with a soap invented by the Mesopotamians. Unfortunately, most soaps are alkali based and rely on consuming the natural skin oils to free up dried or dead skin, dirt, and soil. This strips the skin of natural oils and causes dry skin, flaking and even skin tears, especially in older persons. Liquid cleansers are becoming increasing popular; however, many liquid cleansers do not lather sufficiently well for thorough cleansing. Various cleansing aids such as wash cloths and sponges may impede lathering or even absorb liquid cleansers and moisturizers.

The primary function of human skin is to provide a barrier that contains the other organs of the body. The effectiveness of skin as a barrier depends on its physical integrity, thus, preserving the integrity of healthy skin and restoring the integrity of injured skin are important aspects of maintaining good health. Injuries (burns, cuts, abrasions, incisions) can lead to localized or systemic infection if contaminated; dry skin can lead to pruritis and hasten the formation of skin ulcers (including decubitus ulcers), an especial concern for bedridden patients and the elderly. The normal techniques used in skin cleansing—washing with soap and water, rubbing with sponges and wash cloths—can exacerbate these problems.

The technique of cleansing skin using a basin of water and soap commonly used for bed ridden patients today was popularized by Florence Nightingale over 100 years ago. This technique usually starts with a basin filled with hot water, and involves the use of soap and rough wash cloths to loosen dead skin. Patients are bathed by scrubbing their skin with a well-soaped wash cloth, followed by vigorous towel drying. This technique can easily result in some areas of a patient's body becoming contaminated by bacteria carried from other parts via the washcloth or towel. Another concern is skin damage (abrasions, tears, etc.) due to friction from washcloths and towels, especially in elderly patients and others with fragile, easily-damaged skin.

Most skin cleansing formulations and techniques were developed primarily to remove dirt, soil, and germs carried on the surface of the skin or in the skin's oil, and do little or nothing to protect or enhance the skin or its natural functions. In fact, many sacrifice skin health to achieve the primary objective of skin cleansing.

More recently, substrates pre-moistened with various cleansers, moisturizers, and other additives have been used to provide greater convenience and disposable cleansing systems. For example, Elmore (U.S. Pat. No. 4,220,244) describes a soft cloth pad saturated with salt water and enclosed in a moisture proof envelope having a mirrored surface. The pad can be taken out when needed to refresh and clean the user's face. Toohey (U.S. Pat. No. 4,749,080) teaches a plurality of woven cloths pre-moistened with an aqueous moistening liquid such as pure water, contained in a resealable package. The package is sealed by application of heat and pressure, and sterilized by exposure to gamma radiation. Toohey states that the liquid can contain additives for skin freshening such as alcohol, iodine as an antiseptic, and a skin smoothing agent such as glycerin or lemon oil, altogether not exceeding 10% of the total weight of the aqueous solution.

Some products, such as the delivery system and treatment compositions described by Deckner (U.S. Pat. No. 4,563,346), are designed to air dry after application to the skin. Deckner uses a volatile silicone and a non-ionic lipophilic emulsifier that can be used to deposit a variety of active ingredients on the skin, including oils, humectants, emollients, sunscreens, antiperspirants, and topically active drugs. Other ingredients may include parabens, benzyl alcohol, and imidazolidinyl urea, emollients such as alcohol benzoate, and moisturizers such as panthenol, propylene glycol, or glycerol incorporated into the water phase of the delivery system. The system is said to produce a wash-resistant and sweat-resistant moisturizer film on the skin, which makes it unsuitable for use as a cleanser.

In addition to good cleaning action, cosmetic cleansers should be gentle, causing little or no irritation without drying the skin or leaving it taut. Wivell, et al. (U.S. Pat. No. 5,439,682) provides a personal cleansing and moisturizing composition that includes an anionic surfactant, a long chain C16–22 suspending agent, a dispersed, insoluble oil phase, an additional surfactant, an optional suspending agent, and water. Gordon, et al. (U.S. Pat. No. 5,650,384) combines a hydrophobic, diamond-mesh sponge with a liquid cleansing and moisturizing composition. The composition contains a moisturizing phase and an anionic surfactant in order to clean and moisturize the skin in a single step. Notably, most of the ingredients are rinsed away during use, leaving the relatively heavy, oily moisturizers behind.

Blieszner, et al. (U.S. Pat. No. 5,648,083) teach the addition of a cleansing composition to pre-moistened disposable wipes for personal cleansing of the perineal area. The composition includes water, a protective barrier agent that contains silicone oil, and an emulsifier; it may also include additional components such as pH-adjusting agents, antimicrobial agents, chelating agents, fragrances, skin soothing aids, moisteners, humectants, emollients, and powders. The composition is formulated for use in the normally moist perineal area; thus, repeated use in other, normally-drier areas would cause problems.

Additional compositions and methods are disclosed by Martin, et al. (U.S. Pat. No. 5,702,992), who add an antimicrobial agent to a patient care kit that includes a plurality of cleanser-impregnated cloths packaged in a sealed polyethylene bag. The cleanser is a nonionic, non-rinsing mixture of surfactants, emollients or humectants, vitamin E and deionized water. Williams, et al. (U.S. Pat. No. 4,761,402) describes a soluble, phophorylated glucan composition for treatment of viral and fungal infections; additional ingredients may include antimicrobial agents such as aminoglycoside and gentamicin. The composition is administered in vivo through injection, orally, topically, or by inhalation. Buchalter (U.S. Pat. No. 3,896,807) impregnates an article such as a glove with a therapeutic substance (a non-oily solid which is activated to form a cream upon addition of water or moisture). Murphy's cosmetic product (U.S. Pat. No. 5,653, 967) also includes beta glucan as a suspension agent. The beta glucan is non-toxic and non-irritating, but was not noted to demonstrate any stimulation of macrophages or curative effects.

Many of the substrates used with cleansing compositions are unsuitable for long-term use. For example, paper substrates are biodegradable but abrasive to the skin, and, like dense woven or nonwoven substrates, are ineffective at trapping and carrying away dirt. Unfortunately, most non-woven substrates that are available to consumers are selected for softness and reduced friction without regard for their ability to trap and carry away dirt or soil.

Most known skin cleansing systems contain ingredients that are aimed at producing specific outcomes, but that may also have detrimental side effects. For example, alcohol is fast-drying and kills many varieties of microorganism, but also dries the skin. Iodine, widely used in antiseptic compositions such as Betadine®, is harsh and discolors the skin. Propylene glycol (the main ingredient in antifreeze) is used as a soap, emollient, or preservative, but repeated use and exposure have been found to contribute to contact dermatitis, liver abnormalities, and kidney damage. Mineral oil and other oils may suffocate the skin by forming an oil film; any excess oily residue on the skin surface (including vitamin E) promotes excess sweating which can be detrimental to skin health and maintenance. Sodium lauryl sulfate (SLS) and sodium alureth sulfate (SLES) may cause formation of potentially carcinogenic nitrates and dioxins by reacting with commonly used ingredients found in many products. Glycerin and some other humectants attract and draw in moisture to keep the dead surface skin moist, but when used in quantity can dry out and damage the subsurface, living skin. Other humectants that trap water in solution can damage the skin by over-hydration.

Alcohol, glycerin, and other common ingredients used in cosmetics and skin cleansers are relatively inexpensive at least partly because they have been used in volume in so many different applications for many years. To reduce costs, these ingredients are normally a first choice for new product formulations. Many common ingredients, including propylene glycol and glycerin, are included to impart an impression of silkiness, slipperiness, and other tactile sensations deemed to be desirable to consumers. This poses no significant skin problems for normal usage, or when the product is rinsed off after use. However, many of these popular ingredients are simply inappropriate for repeated use in no-rinse, fast-drying cleansing and moisturizing systems.

Many cosmetic and skin cleansing compositions include antimicrobial agents and preservatives that extend the shelf life of the product (these constituents restrict the growth of microorganisms in the substrate, solution, and container). These constituents are typically selected for their effectiveness in protecting the product rather than their compatibility with human skin or even their effectiveness against microorganisms found on the skin. These constituents are selected for their ability to act relatively slowly during product storage; they are not designed to kill large amounts of microorganisms quickly during skin cleansing, nor are they suitable for leaving on the skin for extended periods of time: an agent that helps prevent the growth of undesired microorganisms during product storage cannot be assumed to be equally effective against bacteria in vivo.

An additional problem is that of cross reactions, which can result in the breakdown of various product constituents and the formation of new compounds that may be harmful to the skin. Many common preservatives are subject to cross reactions, for example, Diazolidinylurea (marketed, inter alia, under the trademarks Germall II or Germaben II) is a broad-spectrum preservative used in cosmetics and pharmaceutical preparations. Diazolidinylurea, which has become a popular constituent of cosmetics, creams and lotions since the early 1980s, is now known to change into formaldehyde if activated to kill microorganisms. When radiated at normal sterilization levels, cross-reactions may change diazolidinylurea into offensive-smelling ammonia or formaldehyde.

Very few products are sterilized as part of, or after the manufacturing process. Instead, manufacturers rely on less costly preservatives matched to known microbial loads on the product to restrict microbial growth during storage. Sterilization is desirable for all skin cleansing products, but especially so for products used in hospitals, nursing homes, extended care facilities, and the like. Contrary to many statements in the prior art literature, presently-available pre-moistened substrates used for skin cleansing typically cannot be adequately sterilized by ultraviolet light, and cannot be ETO-sterilized due to the resulting unallowable levels of ethylene glycol. Gamma or E-beam sterilization is usually unacceptable due to the difficulty in matching multiple ingredients with desired functions that are not significantly altered during required radiation levels. If sterilized by gamma radiation, diazolidinylurea and many other commonly-used ingredients deteriorate, resulting in foul odors or new compounds.

Known skin care compositions rely on pre-cleansing, rinsing, and manually drying the skin, or are intended for temporary skin coatings such as sunscreens and supplemental creams. These compositions are not effective as a one-step, no-rinse cleansing system; their effectiveness is hampered by the problems created during normal pre-cleansing. Furthermore, many presently-available compositions contain ingredients that have harmful side effects. Thus, known skin cleansing systems and compositions rely on a very careful selection of sometimes-incompatible ingredients to prevent unwanted interactions, during storage, during sterilization, and during use. This problem is so common that many—perhaps most—formulations include additional ingredients specifically to help offset the side effects caused by the other ingredients.

Despite the variety of skin cleansing and conditioning systems available to consumers, there is still a need for a practical, cost-effective system based on skin-friendly ingredients. An ideal system would include a non-irritating, lint-free substrate impregnated with a composition that simultaneously cleanses, detoxifies, restructures, and revitalizes the skin, and that air-dries rapidly, leaving a protective film on the skin surface.

SUMMARY OF THE INVENTION

According to its major aspects and broadly stated, the present invention consists of a skin care system that cleanses, therapeutically conditions, and provides additional beneficial treatment to the skin in a simple, one-step application that air dries quickly. (For purposes of this specification, the terms "air dries quickly" and "air dries rapidly" refer to a composition that air dries within approximately two minutes following application to the skin.) The system is implemented as a skin care kit: a container having a plurality of articles therein, each article consisting of a pre-moistened soft cloth. The cloths are impregnated with a treatment composition that contains ingredients selected from the following groups: (a) surfactants, (b) anti-inflammatory agents, (c) non-foaming agents, (d) cell-growth-promoting agents, (e) immune system-enhancing agents, (f) fast-acting antimicrobial agents, (g) absorption facilitating agents or ingredients, (h) humectants and emollients, (i) free radical-scavenging agents, and (j) healing promoting agents. (The terms "agent," "ingredient," and "constituent" are used interchangeably.) The ingredients are further selected to form a stable composition, that is, neither the ingredients nor the composition as a whole deteriorates or undergoes cross reactions when the composition is sterilized by gamma or electron-beam radiation.

In use, the cloths gently cleanse the skin, trap and carry away dirt and soil, and deposit a film of beneficial ingredients that coat and are absorbed into the skin. The system is portable, disposable, easily stored, and can be partially used and resealed for further use. Thus, it is both useful and convenient for medical-related and non-medical skin cleansing.

An important feature of the present invention is the synergistic effect of the selected ingredients. When combined according to the invention, surprisingly low concentrations of these ingredients are needed to provide effective cleansing and moisturizing of the skin, together with delivery of antimicrobial agents that act against local bacteria, viruses, fungi, etc. to help promote healthy skin. The combination of surfactants, humectants, emollients, and other ingredients promotes deeper and more effective absorption of multiple ingredients into the layers of the skin, in a disposable, one-step cleansing and moisturizing system that quickly air dries so that towel drying is not needed.

Another important feature of the present invention is the combination of ingredients used in formulating the composition. In a preferred embodiment, the composition is an aqueous solution that contains approximately 70–90 wt. % water and at least four additional ingredients: at least one ingredient selected from each of groups (a)–(c), and at least one ingredient selected from one of groups (d)–(j). More preferably, the composition contains at least five ingredients in addition to water: at least one ingredient from each of groups (a)–(c), and at least two different ingredients from one of groups (d)–(j). Most preferably, the composition contains at least two different ingredients from each of two different groups (d)–(j) in addition to the ingredients from groups (a)–(c). Additional ingredients such as preservatives and fragrances may be added if desired. The ingredients are selected so as to be compatible with each other, to be radiation-sterilizable, and to provide the desired beneficial treatment.

Another feature of the present invention is the cloths that carry the composition. The cloths are made of a soft, pliable fabric, preferably a fabric that contains at least 50% rayon or other suitable fibers. The structure of the fabric is sufficiently porous (i.e., with a sufficient number of air spaces) that it retains the composition therein during manufacture and storage, but easily releases the composition when wiped gently across the area of skin to be cleansed. The fabric also picks up and carries away dirt, dead skin flakes, and excess skin oils, while depositing a thin layer of the composition on the skin surface.

Other features and advantages of the present invention will be apparent to those skilled in the art from a careful reading of the Detailed Description of Preferred Embodiments presented below and accompanied by the drawings.

DETAILED DESCRIPTION OF PREFERRED EMBODIMENTS

Figure 1:
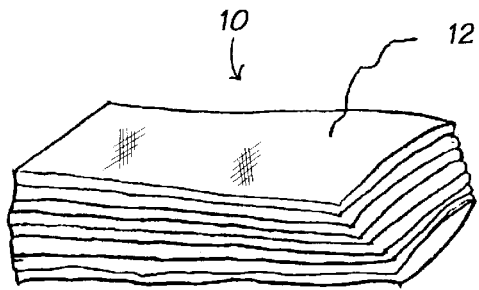
FIG. 1 is a perspective view of a stack of cleanser-impregnated articles according to a preferred embodiment of the present invention.

In the following detailed description of the invention, reference numerals are used to identify structural elements, portions of elements, surfaces or areas in the drawings, as such elements, portions, surfaces or areas may be further described or explained by the entire written specification. For consistency, whenever the same numeral is used in different drawings, it indicates the same element, portion, surface or area as when first used. Unless otherwise indicated, the drawings are intended to be read together with the specification, and are to be considered a portion of the entire written description of this invention as required by 35 U.S.C. §112.

The present invention is a therapeutic skin cleansing, conditioning, and treatment system that includes an article in the form of a soft cloth substrate impregnated with a liquid composition in an amount ranging from approximately 1–6 times the weight of the cloth. The composition itself includes ingredients selected to cleanse, condition, and treat the skin in a one-step application, and preferably includes no more than approximately 20 wt. % active ingredients in water purified by heat, filtration, and/or ultraviolet light. In a preferred embodiment, the invention consists of a pre-packaged kit that contains a plurality of such cleanser-impregnated cloths in a re-sealable container.

Referring now to FIG. 1, there is shown a stack 10 of cleanser-impregnated articles 12 according to the present invention, each article 12 consisting of a cloth substrate impregnated with the above-described composition. The size, weight, and thickness of the individual substrates may vary broadly depending on the intended application. For example, conveniently-sized substrates may range from 0.9–170 g/m$^2$, be cut into 5–36 cm squares or other convenient shapes, and be approximately 0.08–0.2 cm thick (weights and dimensions outside these ranges may also be useful). Smaller cloths are generally useful for cleansing the face or hands, while larger cloths are used for bed baths and the like.

The substrate of articles 12 may be any soft, biologically inert, porous, pliable cloth or fabric that does not interact negatively with the ingredients of the cleansing solution to be described below (for purposes of this detailed description, the terms "cloth" and "fabric" are used interchangeably). The fabric is flexible and at least somewhat loosely woven, with gaps and air pockets that help retain the composition prior to use (during use, these air pockets dispense the composition, and trap and carry away dirt and soil). Overly dense fabrics, regardless of their make-up, lack the air spaces or pockets between the fibers that are needed to hold fluids by cohesion, or to be filled with dirt and soil as the fluids are dispensed. The softer the substrate fabric, the more it is compacted during manufacturing as excess moisture is squeezed out. Thin fabrics, which may be used to reduce bulk and material, packaging, freight, and storage costs, are particularly susceptible to compaction. Therefore, the optimum fabric is best selected in view of its overall weight and structure, and the properties of the composition to be used therewith. Of course, the fabric can be constructed so as to provide the desired absorption rate and release rate for the composition.

The fabric is preferably low lint (i.e., non-pilling), and most preferably nonimmunogenic and nonirritating. Because some individuals may be sensitive to certain fibers, the fabric is preferably made of nonallergenic or hypoallergenic fibers. The fabric itself can be woven or nonwoven, made of needle-punched or hydroentangled fibers, or indeed be made according to any convenient manufacturing technique that produces an end product of sufficient absorbency, air space between fibers, and tensile strength for use with the present invention.

Figure 2A:
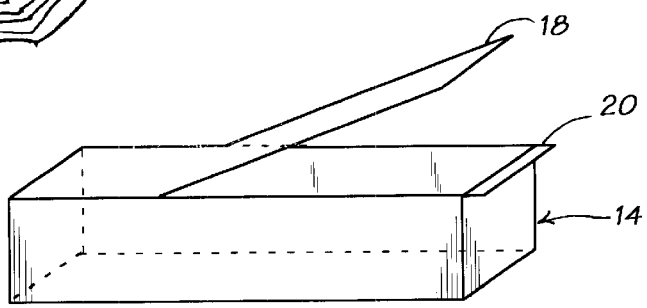
FIGS. 2A and 2B are perspective views of containers usable with the invention.
Figure 2B:
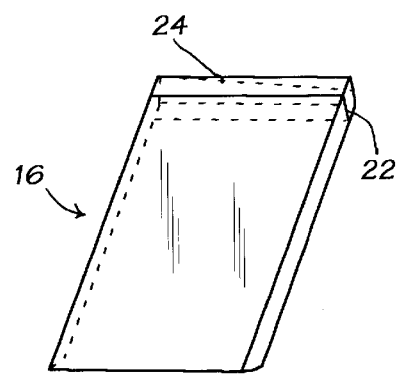

Suitable fibers for use with the invention include, but are not limited to, fibers made of natural materials such as cotton, silk, and combinations thereof Other suitable fibers include rayon, acetate, acrylic, polyethylene, polyester, and so forth. Combinations such as rayon/polyester and cotton/polyester blends (for example, fibers that contain approximately 70% rayon or cotton and 30% polyester). The fabric preferably contains at least approximately 50% rayon, cotton, or blends thereof Articles 12 are packaged in any suitable container, preferably a sterilizable container made of moisture-barrier material. Suitable materials include thermoplastic polymers such as polystyrene, polyester, low density polyethylene, and combinations thereof. Suitable containers include a tray 14 (FIG. 2A) and a bag 16 (FIG. 2B), with walls that need be no more than 0.05–0.25 mm thick. Tray 14 preferably has a heat-sealable lid 18, and a flange 20 at one end that can be grasped by a user and peeled back to open the lid. Bag 16 is formed with a lip 22 with is removed to open the bag. If desired, bag 16 can include a bead-and-groove closure 24 or other recloseable or resealable fastener below lip 22.

Articles 12 carry a composition used for cleansing, conditioning, and treating the skin, made up of a combination of ingredients selected from the following:

(a) Cleansing agents (surfactants and/or soaps), including but not limited to amphoteric surfactants (i.e., surfactants having the capacity of behaving either as an acid or a base), cocamidopropyl betain, alkyl polyglucosides, lauryl glucoside, and combinations thereof While mild soaps are suitable for use with the invention, surfactants are preferred. Surfactants lift soil off the skin by reducing the surface tension, whereas soaps remove protective emollients from the skin and can disturb the normal pH.

(b) Anti-inflammatory agents or agents known to reduce skin reddening, including but not limited to aloe vera, allantoin, cocamidopropyl betain, beta glucan, and combinations thereof, in amounts shown to be effective during cleansing.

Reddened skin is a first sign of infection and other skin problems, and indicates that the skin is redirecting its natural resources from growth and other normal functions to prevention and repair. Reducing or eliminating these distractions significantly increases the growth of healthier new skin.

(c) Skin-compatible anti-foaming agents such as silicone-based antifoaming agents, dimethicone copolyol, and the like.

(d) Agents that stimulate or promote cell growth, including but not limited to aloe vera, allantoin (glyoxyldiureide; 5-ureidohydantoin), beta glucan, polyphenolic compounds such as Citricidal®, and combinations thereof Citricidal® and like compounds have been demonstrated to be effective against a broad spectrum of bacteria. These compounds contain quaternary compounds derived from grapefruit (or other bioflavonoids), together with inert ingredients such as glycerin.

When present in the preferred combinations and concentrations, growth-promoting agents promote or stimulate new skin growth and promote healing of significantly greater magnitude than previously observed.

The above-described ingredients have known beneficial effects. However, the mere presence of these ingredients in a formulation does not automatically result in a product that promotes or assists healing. For example, allantoin is nontoxic, nonirritating, and nonallergenic, and in concentrations of 0.2% or more is known to help in skin healing; it is an FDA-recognized skin protectant in concentrations of 0.5%. However, allantoin easily comes out of solution when present in concentrations exceeding 1%, and must therefore be supported by other similar agents when formulating a composition according to the invention.

It is common practice to add small amounts of aloe vera to cosmetics for its soothing effect as an analgesic (aloe vera contains lignins, saponins, anthraquinones, polysaccharides, and acetylsalicylic acid which blocks the synthesis of prostaglandins). Aloe vera improves wound healing and acts an anti-inflammation agent. However, combining aloe vera as a mannoprotein or polysaccharide with beta glucan in a no-rinse air-drying product such as the invention is believed to be unknown in the prior art.

(e) Agents that enhance and/or stimulate the skin's immune system and/or help provide a secondary immune system, including but not limited to aloe vera, beta glucan, colloidal silver, allantoin, and combinations thereof. When present in the composition in the preferred quantities, these agents promote healing and also help reduce the incidence of infections.

Colloidal silver, Citricidal®, beta glucan, aloe vera, and like ingredients promote and/or stimulate the existing immune system to help reduce infections and promote healing. Colloidal silver and Citricidal® support the natural immune system by reducing its workload; Citricidal® also promotes healing by a mechanism which is as yet unclear.

Beta glucan (a D-glucose polymer also known as beta-1, 3-glucan, beta-1.6-glucan, yeast extract, yeast cell-wall extract, or yeast derivative) is a non-specific immune stimulator that also exhibits free-radical scavenging activity. Beta glucan stimulates the body's immune system T-cells; mannoproteins and polysaccharides such as aloe vera provide the fuel for the T-cells to be effective. A mannoprotein is a sugar-protein (i.e., glycoprotein) that is linked to beta glucan in yeast and barley cell walls. Mannoproteins directly increase the structural integrity, alertness and numbers of immune cells.

(f) Fast-acting, skin-compatible antimicrobial agents (i.e., agents that are effective against bacteria, viruses, yeasts, and/or fungi), including but not limited to colloidal silver, Citricidal®, pycnogenol, grape seed extract, antibiotics, and combinations thereof, in effective amounts to kill infectious bacteria, viruses, yeasts, and fungi on and in the skin during skin cleansing and self drying.

The skin harbors a wide variety of microorganisms; some of these are potentially harmful while others are beneficial. Ideally, this normal bacterial flora is not destroyed by cleansing. However, a cleanser that reduces the accumulation of bacteria, fungi, etc. present on the skin helps reduce the incidence of skin infections, especially in a hospital environment.

The selected antimicrobial agent (or agents) is fast-acting, so as to act against bacteria, fungi, etc. present on the skin surface (in contrast, many prior art products include slow-acting antimicrobial agents and/or preservatives to increase product shelf life). The action of the antimicrobial agent or agents during cleansing and rapid air drying substantially kills viruses, bacteria, fungi, and yeasts present in the living basal cell layer and the dermis of the skin in addition to those transferred onto or living in the dead horny layer or epidermis. This action serves to reduce the occurrence or severity of infections due to bacteria, viruses, etc. entering breaks in the skin (tears, incisions, punctures, abrasions, open wounds, etc.).

Some anti-microbial agents, such as colloidal silver and Citricidal®, are compatible with normal flora, capable of penetrating into the dermis, and also provide useful antimicrobial properties. Colloidal silver kills single-cell microorganisms such as bacteria by penetrating their cell walls in a manner similar to the body's T-cells. Therefore, these organisms cannot mutate into resistant strains as they do with many other antimicrobial agents. However, colloidal silver has limited potency and must preferably be supplemented with other antimicrobial agents in formulating a composition according to the invention. In addition, the colloidal silver is preferably formulated with particles that are small enough to penetrate the dermis (approximately 0.005–0.02 microns; more preferably, approximately 0.01–0.1 microns).

Numerous studies have demonstrated that Citricidal® has many unique and desirable antimicrobial properties, including at least some effectiveness against HIV, hepatitis and other viruses, and a wide range of bacteria, fungi, and yeasts, while being highly biocompatible and providing other benefits to the skin. However, Citricidal® becomes a skin and eye irritant in concentrations greater than approximately 2 wt. %, and has limited effectiveness when used alone at lower concentrations.

Tests of my composition show that a combination of 2% or less Citricidal® and other agents such as colloidal silver is approximately 99.9% or more effective in killing the harmful microorganisms usually present in skin, and prevalent in medical institutions. When present in these low concentrations, these ingredients do not cause skin problems, even when used by volunteers with fragile skin, infections, or problem skin.

(g) Agents that, by their particle size and/or function, facilitate absorption into the second layer of the skin or dermis, including but not limited to beta glucan, aloe vera, colloidal silver, allantoin, Citricidal®, and combinations thereof.

(h) Compatible humectants and emollients, including but not limited to aloe vera, allantoin, vitamin E (tocopherol), beta glucan, cocamidopropyl betain, and combinations thereof These agents naturally re-moisturize the dead horny layer, epidermis, and/or dermis without clogging pores.

Humectants and emollients in the composition act to naturally remoisturize the skin surface (i.e., the dermis) to prevent dryness, increase elasticity, reduce the incidence of skin tears, and supplement the activity of the sebaceous glands to reproduce oils without clogging the pores. Over-usage of humectants and/or emollients is a major cause of skin eruptions, inflammation, and acne, therefore, simply increasing the amounts of humectants and/or emulsifiers to provide a longer lasting protective barrier can promote skin problems. Therefore, the amounts of these ingredients are controlled so as to minimize undesirable effects.

(i) Agents that scavenge free radicals and help detoxify the skin, including but not limited to Citricidal®, beta glucan, allantoin, vitamin E, pycnogenol, grape seed extract, and combinations thereof The composition preferably includes a sufficient quantity of these agent(s) in a form that is delivered deeper than the dead horny layer of the skin in use.

(k) Agents that promote and/or stimulate new skin growth and skin healing, including but not limited to aloe vera, allantoin, Citricidal®, beta glucan, pharmaceuticals, and combinations thereof (k) Biocompatible preservatives, including but not limited to methylparaben, propylparaben, ethylenediamine-tetraacetic acid (EDTA), like agents, and combinations thereof.

(l) Biocompatible fragrances, including but not limited to natural orange, lemon, lavender, and combinations thereof (m) Other beneficial agents, including but not limited to those containing vitamins and vitamin precursors (vitamin A, carotene, cryptoxanthin, retinol, 3-dehydroretinol, vitamin C (ascorbic acid), vitamin E (tocopherol), etc.), herbs (chamomile, lavender, ginseng, ginkgo, etc.), antioxidants, collagens, pH-balancing agents, and combinations thereof Each ingredient of the composition is present in an amount that, as a percentage of the total weight of the composition, is effective either alone or synergistically with the other ingredients to achieve the desired results. By way of example, some of the above-listed ingredients are effective when present in the amounts listed in Table I.

TABLE I

Effective wt. % ranges for selected ingredients usable in a skin cleansing, conditioning and treatment composition according to the present invention.

| Category | Ingredient | Wt. % |
| --- | --- | --- |
| (a) | Aloe vera | 1–7 |
| (b) | Allantoin | 0.2–1 |
| (c) | Cocamidolpropyl betain | 0.2–2 |
| (d) | Lauryl glucoside | 0.1–2 |
| (e) | Dimethicone copolyol | 0.1–2 |
| (f) | Citricidal ® | 0.4–2 |
| (g) | Colloidal silver | 0.2–4 |
| (h) | Beta glucan | 0.1–6 |
| (i) | Methylparaben | 0.1–2 |
| (j) | Propylparaben | 0.1–2 |
| (k) | EDTA | 0.01–0.1 |
| (l) | Fragrances | 0.02–1 |
| (m) | Vitamin E | 0.01–2 |

Selected ingredients of those listed above (or others that provide the same functions) are combined, preferably in aqueous solution, to provide a therapeutic skin cleanser, moisturizing, and treatment system according to the present invention. The ingredients used in the composition are selected to be compatible with each other and with human skin even after exposure to temperatures in the range 0°–140° F., and/or sterilization by gamma or E-beam radiation. All ingredients selected for use in the composition are preferably compatible and gamma-sterilizable, resulting in a stable composition (i.e., a composition that does not degrade or undergo cross-reactions as a result of sterilization).

A composition that contains beta glucan, aloe vera, colloidal silver, and Citricidal® in the above amounts is surprisingly effective in cleansing and treating the skin. The composition air-dries rapidly and promotes increased blood circulation in the treated areas, promoting absorption of beneficial ingredients as the skin equilibrates.

The pH of the composition is preferably relatively close to that of human skin, that is, approximately 4.5–6.7 although compositions with a pH outside this range may also be useful. The composition is naturally pH-balanced when formulated with selected ingredients as described below. However, pH-balancing agents may be added if desired.

A composition according to the invention contains at least one ingredient selected from each of groups (a)–(c) and at least one ingredient selected from one of groups (d)–(j), in aqueous solution. More preferably, the composition includes at least five ingredients in addition to water: at least one ingredient from each of groups (a)–(c), ant at least two different ingredients from one of groups (d)–(j). Most preferably, the composition contains at least two different ingredients, each from a different group of groups (d)–(j). Additional ingredients such as skin-compatible preservatives and fragrances may be added if desired. As used with reference to my composition, the term "antimicrobial agent" refers to fast-acting agents that act against microorganisms present on/in the skin; the term "preservative" refers to relatively slowly-acting agents that help extend the shelf life of the product.

Some ingredients such as aloe vera, allantoin, and beta glucan exhibit a spectrum of useful effects, thus, these ingredients may appear in more than one of above-described groups (a)–(m). However, in a composition formulated according to the invention, each of the selected ingredients is preferably different from the other ingredients so that each selected ingredient is present in sufficient quantity to perform its function or functions. By way of example, if the selected group (b) anti-inflammatory agent is aloe vera, a suitable group (d) ingredient is not aloe vera but rather allantoin or some other agent that stimulates or promotes cell growth. Because the aloe vera may be consumed as an anti-inflammatory agent, it may not be available in sufficient quantity to also promote cell growth, thus, selection of a different cell growth-promoting agent is preferred. Similar considerations apply to all ingredients selected for the composition.

Surprisingly, the combination of group (a)–(c) ingredients with different ingredients selected from group(s) (d)–(j) provides an unexpected, heretofore unobserved level of benefit when used to cleanse and condition the skin. While not wishing to be bound by theory, it is believed that, when combined according to the invention, these ingredients have a synergistic effect that results in more effective skin conditioning and treatment. The effectiveness of the composition results from the combination of different, selected ingredients rather than from any single ingredient (or increased concentrations of any single ingredient). This synergistic effect may be at least partly due to the selection of compatible (including biocompatible) ingredients for the composition that enhance the overall results without producing unwanted side effects or negative skin reactions.

It has been found that a composition that includes aloe vera (a mannoprotein) and water-soluble beta glucan is surprisingly effective in cleansing the skin and stimulating its natural immune system. This unexpected result is believed to be due to the synergism of these two ingredients, when properly combined with the other ingredients of the composition as described above.

The various ingredients in the composition are provided in sufficient quantities and combinations to be effective, and to take advantage of their synergistic effects (when combined according to the invention) without detrimental side effects. Importantly, the composition does not include common ingredients such as alcohol, propylene glycol, SLS, SLES, or others with known deleterious effects. Rather, all of the ingredients of the composition are selected for their overall compatibility with skin health.

The overall effect of the composition is to simultaneously soften and remove some of the outer dead horny layer without stripping the skin of its natural oils, remoisturize the horny layer and the epidermis, and provide some retained moisture to the dermis. It is believed that the low concentrations of active ingredients in the composition, combined with the absence of harsh ingredients and common irritants, serve to reduce the skin's natural immediate response of swelling to restrict entry of any irritating matter. Instead, the compatibility of the ingredients used in formulating the composition promotes replacement of the oils removed during cleansing, and furthers absorption into the dermis of ingredients of sufficiently small particle size.

Those skilled in the art are familiar with the use of preservatives and antimicrobial agents (including timed-release agents) to restrict microbial growth over extended periods of time and thereby increase product shelf life. The present invention differs in that the antimicrobial agents in the composition are selected to meet two criteria: to be compatible with skin health, and to quickly kill harmful microorganisms present on or in the skin. Because of the chemical reactions that may occur when various ingredients are combined, it cannot be assumed that ingredients useful in one formulation will perform a similar function in another formulation, or that antimicrobial agents and preservatives used for increasing product shelf life will be effective against microorganisms found in vivo. As noted above, commonly-used sterilization techniques may increase the likelihood of chemical reactions taking place in the composition; this frequently-neglected phenomenon necessitates careful selection of ingredients and testing of skin care compositions to ensure their stability. Thus, it is crucial to select ingredients that do not interact negatively with each other before, during and after the manufacturing and sterilization processes, and that do not have significant undesired side effects when used on skin. Unlike other skin cleansing compositions known in the art, a composition according to the present invention does not deteriorate as a result of normal sterilization processes.

Figure 3:
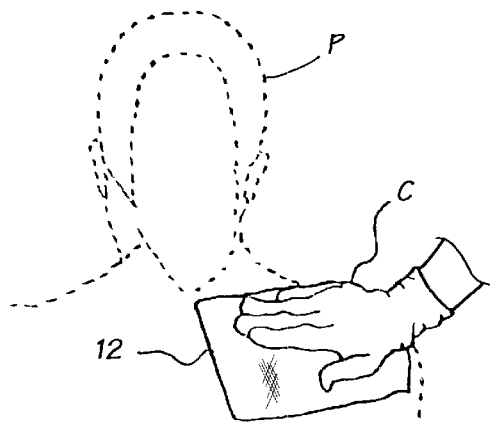
FIG. 3 shows an article according to the invention as typically used to cleanse a person's skin.

In contrast to prior art systems which are aimed at cleansing and moisturizing the skin, my invention cleanses, re-moisturizes, and provides additional skin treatment in a one-step application. When a caregiver C wipes an article 12 gently against the skin of a patient P as shown in FIG. 3, the air pockets in article 12 release the composition and trap and carry away dirt. The preferred usage is to cleanse an area of the skin and carry away the bulk of the solids with one side of an article 12, and then re-wipe with the other side of the article to pick up even more solids, and deposit an amount of the composition.

As noted above, articles 12 contain the above-described composition in the amount of approximately 1–6 times the weight of the fabric substrate. When wiped gently or patted against the skin, an article 12 easily releases at least some of the composition contained therein with minimal dripping. The composition cleanses the skin with gentle surfactant soaps that reduce inflammation and skin redness. (Surfactants separate dirt, soil, and body oils by reducing surface tensions, unlike alkali soaps that consume body oils to free up dirt and soil. Thus, the skin is not stripped and dried but rather is remoisturized and treated with beneficial ingredients.) The composition also soothes, softens and moisturizes the skin, leaving a residue that quickly air-dries and acts as a barrier to pollutants that nevertheless allows the skin to breathe naturally. Indeed, some of the ingredients are believed to be absorbed into the dermal layer of the skin. This deep absorption of ingredients, selected for their ability to penetrate the epidermis to reach the dermis, promotes deep healing, and new or enhanced synergistic effects. A table showing some of the differences in therapeutic benefits and ingredients provided by the invention and prior art cleansing systems is shown in Table II.

TABLE II

Benefits provided by the traditional basin bed bath, a newer basinless bed bath, and a new bed bath according to the present invention.

| Benefit | Traditional Basin Bed Bath | Basinless Bed Bath | New Bed Bath |
| --- | --- | --- | --- |
| Cleans skin surface | Yes | Yes | Yes |
| Leaves skin clean with minimal re-dried soil | No | Maybe | Yes |
| Maintains normal skin pH | No | Maybe | Yes |
| Reduces time needed to prepare, give, and clean up after bath | No | Yes | Yes |
| Remoisturize during skin cleansing makes skin surface feel moist | No | Yes | Yes |
| re-moisturizes skin with compatible ingredients | No | Maybe | Yes |
| effectively moisturizes two or more skin layers | No | No | Yes |
| Applies a moisture barrier during cleansing | No | Yes | Yes |
| using agents compatible with normal skin functions | No | No | yes |
| Formulation combines agents to deliver additional benefits during skin cleansing, selected from the following: | | | |
| (a) agents in sufficient quantity to significantly reduce levels of harmful bacteria, viruses, fungi, and yeasts on or in the skin | Maybe | Maybe | Yes |
| using one or more agents compatible with the skin's natural functions | No | No | Yes |
| (b) agents that effectively promote healing of cuts, abrasions, and burns | No | No | Yes |
| (c) agents that effectively reduces skin redness or inflammation | No | No | Yes |
| (d) agents that effectively promote cell renewal or growing new skin faster | No | No | Yes |
| (e) agents that effectively enhances the skin's natural immune system and/or provides a secondary immune system | No | No | Yes |
| (f) agents that scavenge free radicals to detoxify the skin | No | No | Yes |
| (g) Makes the skin feel cool, refreshed, or invigorated | No | No | Yes |

The operation of the present invention is further illustrated by the following non-limiting examples.

EXAMPLE 1

Test organisms (*Escherichia coli* (*E. coli*), Staphylococcus aureus (S. aureus), *Candida albicans* (*C. albicans*)) were grown overnight in Trypticase-soy broth at 35° C., then diluted in distilled water immediately before product challenge. The initial inoculum density was determined using the standard plate count method.

Diluted cell suspensions (100 µl) of a selected test organism was directly inoculated into six 900-µl preparations of the test product (a composition having the ingredients listed in Table I above). Products 4–6 contained approximately twice as much of the selected antimicrobial agent as products 1–3.

At selected time intervals (5, 15, 20, and 60 minutes), 100-µl aliquots were removed from each test product and aseptically transferred to the surface of a D/E Neutralizing agar recovery medium. The recovery medium was incubated at 35° C. for 48 hours and evaluated for microbial survival. Test results are shown in Table III.

TABLE III

Antimicrobial activity of a composition according to the present invention.

| | | | # Surviving Cells (CFU/Plate) | | | |
| --- | --- | --- | --- | --- | --- | --- |
| Product No. | Test Organism | Initial Inoculum (CFU/Swatch) | 5 min. | 15 min. | 30 min. | 60 min. |
| 1 | E. coli | $2.32 \times 10^3$ | 0 | 0 | 0 | 0 |
| 2 | S. aureus | $1.06 \times 10^3$ | 0 | 0 | 0 | 0 |
| 3 | C. albicans | $1.06 \times 10^3$ | 0 | 0 | 0 | 0 |
| 4 | E. coli | $2.32 \times 10^3$ | 0 | 0 | 0 | 0 |
| 5 | S. aureus | $1.06 \times 10^3$ | 0 | 0 | 0 | 0 |
| 6 | C. albicans | $1.06 \times 10^3$ | 0 | 0 | 0 | 0 |

All six products exhibited strong, rapid antibacterial activity against the tested microorganisms, reducing viable cell populates by >99.9% in 5 minutes.

EXAMPLE 2

A quantity of soft, lint-free cloth was impregnated with a composition that contained approximately 20 wt. % active ingredients (aloe vera, allantoin, cocamidopropyl betain, lauryl glucoside, dimethione copolyol, beta glucan, vitamin E, antimicrobial preservatives, and fragrance) in pure water. The cloth was cut into six 1"-square swatches which were placed into sterile, disposable Petri dishes. Swatches 4–6 contained approximately twice as much of the selected antimicrobial agent as swatches 1–3.

Test organisms were prepared as described in Example 1 above. Each swatch was inoculated with a selected test organism and incubated at room temperature for a selected time interval (5, 15 min., 30., or 60 minutes). After incubation, each swatch was aseptically transferred to a sterile stomacher bag containing 10 ml of a peptone-tween 80 extraction fluid and homogenized for 3 minutes at room temperature. The extracting fluid was then assessed for the number of surviving cells using membrane filtration. Test results are shown in Table IV.

TABLE IV

Antimicrobial activity of 1"-square cloth swatches
impregnated with a composition according to the present invention.

| Swatch No. | Test Organism | Initial Inoculum (CFU/Swatch) | # Surviving Cells (CFU/Swatch) | | | |
|---|---|---|---|---|---|---|
| | | | 5 min. | 15 min. | 30 min. | 60 min. |
| 1 | E. coli | 8300 | 18 | 2 | 16 | 2 |
| 2 | S. aureus | 3300 | >300 | 284 | 92 | 12 |
| 3 | C. albicans | 4950 | <2 | <2 | <2 | <2 |
| 4 | E. coli | 8300 | <2 | <2 | <2 | <2 |
| 5 | S. aureus | 3300 | 102 | 22 | <2 | <2 |
| 6 | C. albicans | 4950 | <2 | <2 | <2 | <2 |

The tested composition exhibited strong antibacterial activity against *E. coli* and *C. albicans*, with a lesser degree of activity against *C. albicans*. Swatches 4–6, which contained approximately twice as much of the antimicrobial agent as swatches 1–3, exhibited a correspondingly greater degree of antibacterial activity against all three microorganisms tested. This effect was especially evident in the case of *S. aureus* (swatches 2 and 5).

EXAMPLE 3

A plurality of articles 12 were made by impregnating soft, lint-free gauze cloths with a composition having the ingredients listed in Table I above. The composition was an aqueous solution that contained approximately 20 wt. % active ingredients (aloe vera, allantoin, cocamidopropyl betain, lauryl glucoside, dimethione copolyol, beta glucan, vitamin E, antimicrobial preservatives, and fragrance) in pure water. The cleanser-impregnated articles 12 were packaged in resealable bags and sterilized with gamma radiation.

After opening, articles 12 were used as a facial cleanser and conditioner. The articles were effective in removing makeup, and in moisturizing and generally toning the skin. Tests by a dermatologist showed that articles 12 were non-irritating to the skin, even when used on problem skin and previously-irritated skin.

Compositions which contain beta glucan, Citricidal® and colloidal silver, such as the composition of Example 3, were found to be faster-drying than compositions without these three ingredients. This effect is believed to be due to enhanced delivery of smaller particle nutrients in the composition to the dermis and/or to the basal cell layer of the skin. Compositions with these ingredients were also found to calm red and inflamed sebaceous glands and razor burn more rapidly than those without these ingredients.

The system of the present invention is portable, disposable, and easy to use. Articles 12 are packed in a recloseable container such as a tray, bag or envelope for easy storage, with each container preferably holding a sufficient number of articles for a full bath. Thus, when used for facial cleansing or spot cleansing, the used article can be discarded and the others saved for later use.

Figure 4:
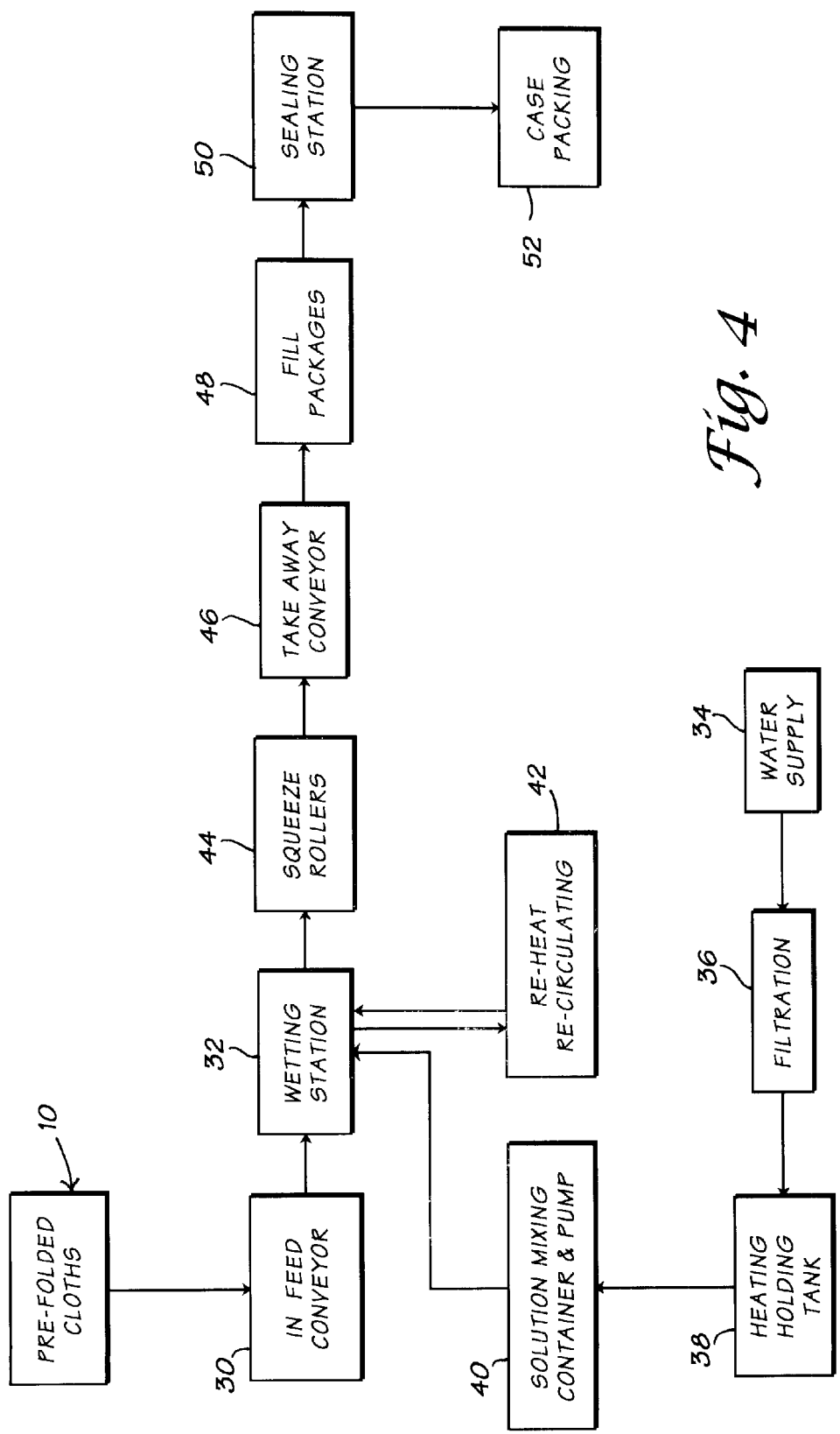
FIG. 4 is a flow diagram of a process for manufacturing and assembling a kit according to the invention.

A system according to the invention can be manufactured by any convenient method, including but not limited to the method outlined schematically in FIG. 4. Here, a stack 10 containing a selected number of pre-folded dry substrates or cloths is placed on an infeed conveyor belt 30. Conveyor belt 30 transports stack 10 to a wetting station 32, which consists of a trough, a top or hold-down conveyor belt, and a pathway along the bottom of the trough for conveyor belt 30 and stack 10 (not shown). Conveyor belts used for in the manufacturing process are preferably made of open links to allow liquid to freely pass through them.

Water from a main supply 34 is passed through a filtration and purification system 36 that purifies the water by removing chlorine, heavy metals, particles larger than approximately 0.5 microns, and by passing through an ultraviolet light. The filtered water is pre-heated to a temperature of about 110°–140° F. in a heating and holding tank 38. Pre-heated purified water is pumped from tank 38 to a solution mixing tank 40, filling it to a predetermined batch size level.

A batch of the above-described composition is prepared by adding corresponding amounts of each selected ingredient to achieve a predetermined percent by weight of each ingredient in the final composition. The selected ingredients are added to mixing tank 40 by any convenient techniques, and mixed in by an internal re-circulating pump.

Preferably, the ingredients are added in decreasing order of each ingredient's need for heat to disperse or dissolve into the solution until the predetermined solution or formulation is achieved. That is, ingredients that dissolve or disperse more readily in warmer solutions are added first, followed by ingredients that dissolve or disperse easily in cooler solutions. Batches of the composition are typically made within one hour of use in production. For convenience, mixing tank 40, containing a batch of the composition, can be can be removed and replaced with a second such mixing tank for a semi-continuous production process.

A selected amount of the composition is pumped from mixing tank 40 to wetting station 32 (as determined by a fluid level sensor in station 32, or other suitable monitoring device). Stack 10 is held in position by the hold-down belt of wetting station 32, and controlled and transported through the composition by the combined effect of the top and bottom belts moving downstream at matched speeds. Stack 10 is fully saturated with the composition as it passes through wetting station 32, resulting in a stack of articles 12 as described above. To replace the composition added to stack 10, a replacement amount of the composition is pumped to wetting station 32 (as called for by a fluid level sensor or other suitable monitoring and/or metering device). The ingredients of the composition are kept in solution by agitation of the top and bottom conveyor belts moving through the composition, and by constantly re-circulating the composition through an auxiliary heating system and back to the trough of wetting station 32. An auxiliary re-heating and re-circulating system 42 uses an internal thermostat to maintain the composition at a selected temperature, for example, a temperature in the range of approximately 110–140° F.

Stack 10 is then fed by the conveyor belts to a set of squeeze rollers 44, which are preset to achieve a targeted range of retention weight of the composition in the articles 12 of the stack. The pre-moistened weights of stacks 10 are periodically checked, and squeeze rollers 44 are adjusted as required to maintain the solution target weights. Stack 10 exits squeeze rollers 44 onto a take away conveyor 46 for presentation to a fill package station 48. Here, one or more stacks 10 are placed into a selected container (tray, bag, envelope, box, package, etc.) to form a kit with a preselected count of articles 12. The filled containers are presented to a sealing station 50 and sealed, then transferred to a packing station 52 where the containers are packaged in boxes for shipment. It will be evident that other manufacturing processes can also be used to produce the invention, provided that articles 12 are pre-moistened with the composition in a suitable weight range.

The ingredients of the above-described composition have an unexpected combination of beneficial effects, including cleansing, conditioning, and treatment. The ingredients are selected so that at least some combination thereof penetrates the skin into the dermis during and immediately after cleansing. There is a highly synergistic effect produced by simultaneously not stripping most of the natural skin oils/waxes, softening and removing some of the dead horny layer, re-moisturizing the dead horny layer and the epidermis, and providing some retained moisture to the dermis. In addition, the fast-acting antimicrobial agent (or agents) in the composition act against viruses, bacteria, fungi, and yeasts present in the living basal cell layer and dermis, in addition to those transferred onto or living in the dead horny layer or epidermal layers of the skin. This action reduces the occurrence or severity of infections due to these microorganisms entering breaks in the epidermis (tears, abrasions, incisions (including incisions for placement of catheters and stitches), and sores). This deep absorption of ingredients, selected for their ability to penetrate the epidermis to reach the dermis, helps promote deep healing and overall skin health.

A skin cleansing, conditioning, and treatment system according to the present invention offers both ease of use and synergistic effects. In use, the system minimizes skin damage or impairment of natural skin functions during cleansing which may result from the action of some of the ingredients (or combinations of ingredients) found in many cleansing compositions available to consumers. It delivers these ingredients where needed in a simple, one-step application procedure, thereby promoting improved skin care by making it more convenient, economical, faster, not only for home use but also in hospitals and nursing homes whose clients require bedside bathing. The system is portable, disposable, and can be partially used and restored for further use. This makes it useful and convenient for both medical-related (i.e., in hospitals, nursing homes, and extended care facilities), and non-medical (make-up removal, general skin cleansing and conditioning). Importantly, the invention provides skin cleansing and treatment in accordance with the U.S. Department of Health and Human Services May 1992 Clinical Practice Guideline Number 3 for prevention of pressure ulcers in adults.

The above-described composition deep-cleanses the skin, and, depending on the particular selection of ingredients, replaces dead skin, germs, soil, and partially decomposed body oil or sebum with nutrients, anti-microbial agents, immune system builders, and other natural skin function stimulators that promote cell growth and healing, reduce inflammation, and reduce skin redness. The formulation of the composition, which in a preferred embodiment has multiple ingredients having similar or related benefits, promotes synergistic effects: the composition as a whole is more effective than each individual ingredient if used separately. This combination of ingredients has cleansing, preventative and curative properties that enhance skin recovery and maintenance, and reduce harmful effects due to outside stimuli, and organisms.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. A liquid composition for use in cleansing the skin, said composition comprising an aqueous solution containing:
    (a) at least one surfactant;
    (b) at least one anti-inflammatory agent;
    (c) at least one anti-foaming agent;
    (d) at least one cell growth-promoting agent;
    (e) at least one immune system-enhancing agent;
    (f) at least one fast-acting, skin-compatible antimicrobial agent;
    (g) at least one absorption facilitating agent;
    (h) at least one humectant or emollient;
    (i) at least one free radical-scavenging agent; and
    (j) at least one healing promoting agent, wherein said agents are selected to form a stable composition that cleanses, therapeutically conditions, and treats the skin in a one-step application, wherein each of said agents differs from the other agents in said composition, and wherein said composition contains, by weight, approximately 1–7% (a), 0.2–1% (b), 0.2–2% (c), 0.1–2% (d), 0.1–2% (e), 0.4–2% (f), 0.2–4% (g), 0.1–6% (h), 0.1–2% (i), and 0.1–2% (j).

2. The composition as recited in claim 1, further comprising at least one skin-compatible preservative.

3. The composition as recited in claim 1, further comprising at least one fragrance.

4. The composition as recited in claim 1, wherein said composition contains approximately 70–90 wt. % water.

5. The composition as recited in claim 1, wherein said at least one surfactant (a) is an amphoteric surfactant;
    wherein said at least one anti-inflammatory agent (b) is aloe vera, allantoin, or cocamidopropyl betain; and
    wherein said at least one anti-foaming agent (c) is skin-compatible.

6. The composition as recited in claim 1, wherein said at least one cell growth-promoting agent (d) is aloe vera, allantoin, beta glucan, a bioflavonoid, a polyphenolic compound, or a grapefruit-derived quaternary compound;
    wherein said at least one immune system-enhancing agent (e) is aloe vera, beta glucan, colloidal silver, or allantoin;
    wherein said at least one antimicrobial agent (f) is colloidal silver, a bioflavonoid, a polyphenolic compound, a grapefruit-derived quaternary compound, pycnogenol, or grape seed extract;
    wherein said at least one absorption facilitating agent (g) is beta glucan, aloe vera, or colloidal silver;
    wherein said at least one humectant or emollient (h) is aloe vera, vitamin E, or cocamidopropyl betain;
    wherein said at least one free radical-scavenging agent (i) is a bioflavonoid, a polyphenolic compound, a grapefruit-derived quaternary compound, beta glucan, allantoin, vitamin E, pycnogenol, or grape seed extract; and wherein said at least one healing-promoting agent (j) is aloe vera, allantoin, or beta glucan.

7. The composition as recited in claim 2, wherein said at least one preservative includes methylparaben, propylparaben, EDTA, or mixtures thereof.

8. The composition as recited in claim 1, wherein said composition contains, by weight, approximately 1–7% (a), 0.2–1% (b), 0.2–2% (c), 0.1–2% (d), 0.1 2% (e), 0.4–2% (f), 0.2–4% (g), 0.1–6% (h), 0.1–2% (i), and 0.1–2% (j).

9. The composition as recited in claim 1, wherein said at least one surfactant is a cleanser.

10. A method for cleansing, conditioning, and treating the skin, said method comprising applying to the skin a liquid composition comprising an aqueous solution containing the ingredients:
- (a) at least one surfactant;
- (b) at least one anti-inflammatory agent;
- (c) at least one anti-foaming agent;
- (d) at least one cell growth-promoting agent;
- (e) at least one fast-acting antimicrobial agent, each of said ingredients being skin-compatible and different from the other ingredients of said composition; and
at least one different ingredient selected from the group of:
- (f) immune system-enhancing agents;
- (g) absorption facilitating agents;
- (h) humectants and emollients;
- (i) free radical-scavenging agents; and
- (j)healing promoting agents, wherein said ingredients are selected to form a stable, no-rinse, radiation-sterilizable composition that air-dries quickly when applied to the skin, that cleanses, therapeutically conditions, and treats the skin in a one-step application.

11. The method as recited in claim 10, wherein said least one immune system-enhancing agent (f) is aloe vera, beta glucan, colloidal silver, or allantoin;
wherein said at least one absorption facilitating agent (g) is beta glucan, aloe vera, or colloidal silver;
wherein said at least one humectant or emollient (h) is aloe vera, vitamin E, or cocamidopropyl betain;
wherein said at least one free radical-scavenging agent (i) is a bioflavonoid, a polyphenolic compound, a grapefruit-derived quaternary compound, beta glucan, allantoin, vitamin E, pycnogenol, or grape seed extract; and
wherein said at least one healing-promoting agent (j) is aloe vera, allantoin, or beta glucan.

12. The method as recited in claim 10, further comprising at least one ingredient selected from the group consisting of skin-compatible preservatives and fragrances.

13. The method as recited in claim 10, wherein said composition contains approximately 70–90 wt. % water.

14. The method as recited in claim 10, wherein said at least one surfactant (a) is an amphoteric surfactant.

15. The method as recited in claim 10, wherein said at least one surfactant (a) is a cleanser.

16. The method as recited in claim 10, wherein said at least one anti-inflammatory agent (b) is aloe vera, allantoin, or cocamidopropyl betain;
wherein said at least one cell growth-promoting agent (d) is aloe vera, allantoin, beta glucan, a bioflavonoid, a polyphenolic compound, or a grapefruit-derived quaternary compound; and
wherein said at least one antimicrobial agent (c) is colloidal silver, a bioflavonoid, a polyphenolic compound, a grapefruit-derived quaternary compound, pycnogenol, or grape seed extract.

17. The method as recited in claim 10, wherein said composition contains, by weight, approximately 1–7% (a), 0.2–1% (b), 0.2–2% (c), 0.1–2% (d), 0.1–2% (e), 0.4–2% (f), 0.2–4% (g), 0.1–6% (h), 0.1–2% (i), and 0.1–2% (j).

18. An article for use in cleansing the skin, said article comprising:
a fabric substrate; and
an aqueous solution carried by said fabric substrate, said aqueous solution containing the ingredients
- (a) at least one surfactant,
- (b) at least one anti-inflammatory agent,
- (c) at least one anti-foaming agent,
- (d) at least one cell growth-promoting agent;
- (e) at least one fast-acting antimicrobial agent;
- (f) at least one immune system-enhancing agent,
- (g) at least one absorption facilitating agent;
- (h) at least one agent selected from the group of humectants and emollients,
- (i) at least one free radical-scavenging agent; and
- (j) at least one healing promoting agent, each of said ingredients being skin-compatible and different from the other ingredients of said aqueous solution, wherein said ingredients are selected to form a stable composition that air-dries quickly when applied to the skin, and that cleanses, therapeutically conditions, and treats the skin in a one-step application, and wherein said composition contains, by weight, approximately 1–7% (a), 0.2–1% (b), 0.2–2% (c), 0.1–2% (d), 0.1–2% (e), 0.4–2% (f), 0.2–4% (g), 0.1–6% (h), 1–2% (i), and 0.1–2% (j).

19. The article as recited in claim 18, wherein said aqueous solution further comprises at least one different ingredient selected from the group of:
- (f) immune system-enhancing agents;
- (g) absorption facilitating agents;
- (h) humectants and emollients;
- (i) free radical-scavenging agents; and
- (j) healing promoting agents.

20. The article as recited in claim 19, wherein said at least one immune system-enhancing agent (f) is aloe vera, beta glucan, colloidal silver, or allantoin;
wherein said at least one absorption facilitating agent (g) is beta glucan, aloe vera, or colloidal silver;
wherein said at least one humectant or emollient (h) is aloe vera, vitamin E, or cocamidopropyl betain;
wherein said at least one free radical-scavenging agent (i) is a bioflavonoid, a polyphenolic compound, a grapefruit-derived quaternary compound, beta glucan, allantoin, vitamin E, pycnogenol, or grape seed extract; and
wherein said at least one healing-promoting agent (j) is aloe vera, allantoin, or beta glucan.

21. The article as recited in claim 18, wherein said aqueous solution further comprises at least one ingredient selected from the group consisting of skin-compatible preservatives and fragrances.

22. The article as recited in claim 18, wherein said at least one anti-inflammatory agent (b) is aloe vera, allantoin, or cocamidopropyl betain;
wherein said at least one cell growth-promoting agent (d) is aloe vera, allantoin, beta glucan, a bioflavonoid, a polyphenolic compound, or a grapefruit-derived quaternary compound; and wherein said at least one antimicrobial agent (e) is colloidal silver, a bioflavonoid, a polyphenolic compound, a grapefruit-derived quaternary compound, pycnogenol, or grape seed extract.

23. The article as recited in claim 18, wherein said aqueous solution contains, by weight, approximately 1–7% (a), 0.2–% (b), 0.2–2% (c), 0.1–2% (d), 0.1–2% (e), 0.4–2% (f), 0.2–4% (g), 0.1–6% (h), 0.1–2% (i), and 0.1–2% (j).

24. The article as recited in claim 18, wherein said fabric substrate is made of a material selected from the group consisting of cotton, silk, rayon, acetate, acrylic, polyethylene, polyester, and mixtures and blends thereof.

25. A kit for use in cleansing the skin, said kit comprising:
a container; and
a plurality of articles in said container, each of said articles comprising
a fabric substrate, and
an aqueous solution carried by said fabric substrate, said aqueous solution containing the ingredients
(a) at least one surfactant,
(b) at least one anti-inflammatory agent,
(c) at least one anti-foaming agent,
(d) at least one cell growth-promoting agent;
(e) at least one fast-acting antimicrobial agent;
(f) at least one immune system-enhancing agent;
(g) at least one absorption facilitating agent;
(h) at least one agent selected from the group of humectants and emollients;
(i) at least one free radical-scavenging agents; and
(j) at least one healing promoting agent, each of said ingredients being skin-compatible and different from the other ingredients of said aqueous solution, wherein said ingredients are selected to form a stable composition that air-dries quickly when applied to the skin, and that cleanses, therapeutically conditions, and treats the skin in a one-step application, and wherein said composition contains, by weight, approximately 1–7% (a), 0.2–1% (b), 0.2–2% (c), 0.1–2% (d), 0.1–2% (e), 0.4–2% (f), 0. 2–4% (g), 0.1–6% (h), 0.1–2% (i), and 0.1–2% (j).

26. The kit as recited in claim 25, wherein said at least one anti-inflammatory agent (b) is aloe vera, allantoin, or cocamidopropyl betain;
wherein said at least one cell growth-promoting agent (d) is aloe vera, allantoin, beta glucan, a bioflavonoid, a polyphenolic compound, or a grapefruit-derived quaternary compound; and
wherein said at least one antimicrobial agent (e) is colloidal silver, a bioflavonoid, a polyphenolic compound, a grapefruit-derived quaternary compound, pycnogenol, or grape seed extract.

27. The kit as recited in claim 25, wherein said at least one immune system-enhancing agent (f) is aloe vera, beta glucan colloidal silver, or allantoin;
wherein said at least one absorption facilitating agent (g) is beta glucan, aloe vera, or colloidal silver,
wherein said at least one humectant or emollient (h) is aloe vera, vitamin E, or cocamidopropyl betain;
wherein said at least one free radical-scavenging agent (i) is a bioflavonoid, a polyphenolic compound, a grapefruit-derived quaternary compound, beta glucan, allantoin, vitamin E, pycnogenol, or grape seed extract; and
wherein said at least one healing-promoting agent (j) is aloe vera, allantoin, or beta glucan.

28. The kit as recited in claim 25, wherein said aqueous solution further comprises at least one ingredient selected from the group consisting of skin-compatible preservatives and fragrances.

29. The kit as recited in claim 25, wherein said fabric substrate is made of a material selected from the group consisting of cotton, silk, rayon, acetate, acrylic, polyethylene, polyester, and mixtures and blends thereof.

30. The composition as recited in claim 10, wherein said composition contains, by weight, approximately 1–7% (a); 0.2–1% (b); 0.2–2% (c); 0.1–2% (d); 0.1–2% (e); and 0.4–2% (f), 0.2–4% (g), 0.1–6% (h), 0.1–2% (I), or 0.1–2% (j).

* * * * *